United States Patent [19]

Kalbe et al.

[11] Patent Number: 5,717,087

[45] Date of Patent: Feb. 10, 1998

[54] THERMOPLASTIC AND BIODEGRADABLE POLYSACCHARIDE ESTERS/ POLYSACCHARIDE ETHER ESTERS CONTAINING MALEIC ACID ADDITION PRODUCT GROUPS

[75] Inventors: Jochen Kalbe, Essen; Reinhard Koch, Köln; Hanns Peter Müller, Odenthal; Jürgen Engelhardt, Fallingbostel; Wolfgang Koch; Volkhard Müller, both of Bomlitz, all of Germany

[73] Assignee: Wolff Walsrode AG, Walsrode, Germany

[21] Appl. No.: 692,028

[22] Filed: Aug. 2, 1996

[30] Foreign Application Priority Data

Aug. 10, 1995 [DE] Germany .................. 195 29 409.2

[51] Int. Cl.⁶ .................. C08B 13/00; C08B 31/04
[52] U.S. Cl. .................. 536/32; 536/33; 536/48; 536/49; 536/58; 536/59; 536/63; 536/64; 536/65; 536/66; 536/68; 536/69; 536/108; 536/109; 536/110; 424/488; 427/391
[58] Field of Search .................. 536/32, 33, 48, 536/49, 58, 59, 63, 64, 65, 66, 68, 69, 108, 109, 110; 424/488; 427/391

[56] References Cited

U.S. PATENT DOCUMENTS

| | | | |
|---|---|---|---|
| 2,661,349 | 12/1953 | Caldwell et al. | 260/224 |
| 5,459,258 | 10/1995 | Merrill et al. | 536/123 |
| 5,466,794 | 11/1995 | Kalbe et al. | 536/66 |

FOREIGN PATENT DOCUMENTS 0 626 392 A1   11/1994   European Pat. Off. .

*Primary Examiner*—Frederick Krass
*Attorney, Agent, or Firm*—Sprung Kramer Schaefer & Briscoe

[57] ABSTRACT

The present invention relates to thermoplastic and biodegradable polysaccharide esters/polysaccharide ether esters, which are characterised in that they can be represented by the general structure

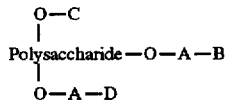

wherein Polysaccharide-O represents the substituted OH groups of a polymeric saccharide unit and wherein A is a linear polyether chain of the following structure $$A = (E-O)_n$$

wherein E signifies a linear aliphatic or aromatic branched or unbranched chain having 2 to 11 C atoms, n is an integer equal to or greater than 0 and both B and D are a maleic acid addition product of the following structure

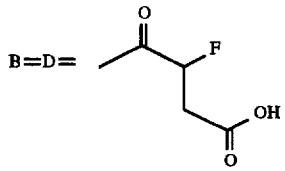

wherein F is an aliphatic, saturated, monounsaturated or polyunsaturated carbon skeleton, which may optionally be provided with further substituents and wherein C can be a hydrogen atom, one or more substituents from the group dihydroxyethyl, hydroxypropyl, hydroxybutyl, methyl, ethyl, benzyl, dihydroxypropyl, carboxyalkyl, sulphoalkyl or cyanoethyl.

11 Claims, No Drawings

THERMOPLASTIC AND BIODEGRADABLE POLYSACCHARIDE ESTERS/ POLYSACCHARIDE ETHER ESTERS CONTAINING MALEIC ACID ADDITION PRODUCT GROUPS

The present invention relates to novel thermoplastic and biodegradable polysaccharide esters/polysaccharide ether esters such as, for example, starch esters, starch ether esters and cellulose ether esters, and the preparation of these polysaccharide esters/polysaccharide ether esters from maleic acid addition products such as, for example, alkyl- and/or alkenylsuccinic acid, in addition mixed esters of polysaccharides/polysaccharide ethers which contain as ester components maleic acid addition products and other dicarboxylic acid or monocarboxylic acid groups.

Cellulose ether esters described in the literature are composed of cellulose ethers which are converted to their monoesters by various methods using carboxylic anhydrides. [See C. J. Malta, Analytical Chemistry, 25 (2), 1953, 245–249; C. J. Malta, Industrial and Engineering Chemistry, 49 (1), 1957, 84–88; EP 0 219 426 (06.10.86), DOS 2 140 996 (16.08.71)].

Different types of mixed monocarboxylic esters and dicarboxylic esters of cellulose or cellulose ethers such as, for example, cellulose acetate phthalate (Publication No. ZFD-101 B of the firm Eastman Chemical Products Inc., USA, 1975 and G. T. Luce in Pharmaceutical Technology, June 1977), cellulose acetate succinate [J. of Pharm. Sci., 51, 1962, 484; Chem. Abstr. 76, 1972, 125, Ref. 129 046 t; Chem. Abstr. 81, 1974, 143, Ref. 154 839 q] and hydroxypropyl cellulose acetate succinate [EP 0 219 426 (06.10.86)] have also been known for a long time.

According to requirements, sets of properties can be established by varying the ether derivative, for example, methyl, ethyl, hydroxyethyl, hydroxypropyl, propyl, butyl cellulose, or else mixed ether types such as methylhydroxyethyl or methylhydroxypropyl cellulose, or by choosing different dicarboxylic anhydrides such as, for example, those of phthalic acid, tetrahydrophthalic acid, hexahydrophthalic acid, succinic acid, or by varying the degree of substitution of these substituents [see DE OS 2 140 996 (16.08.71), EP 0 219 426 (06.10.86)].

These classes of products are coating systems which can be applied from organic solvents or from water for the encapsulation of tablets, or antihalation coatings.

The biodegradability of a polysaccharide derivative is dependent on the level of the degree of substitution of each saccharide unit [see J. G. Batelaan in The Handbook of Environmental Chemistry, Volume 3, Part F, Ed. O. Hutzinger, Springer Verlag, 1992, 229–336, M. G. Wirick, Journal of Polymer Science, Part A-1, 6 (1968), 1705–1718]. Thus all industrially available cellulose derivatives are readily biodegradable only at average degrees of substitution of less than 1.0. In comparison, thermoplasticity is attained only at degrees of substitution of more than 2.5 in known derivatives such as, for example, cellulose acetate (T. Eicher, in Ullmanns Encyklopädie der technischen Chemie, 4th edition, 9, 1975, 227–246).

The generally readily biodegradable, relatively unmodified polysaccharides cannot therefore satisfy technological requirements such as, for example, extrudability in conventional extruders, nor requirements such as moisture resistance and impermeability to water and show no mechanical properties comparable with those of standard plastics [K. Dormann, Zuckerind. 116 (7), 191, 620–623].

There are thus no cellulose derivatives which are thermoplastic and hence also capable of being extruded to form moulded parts, for example sheets, and which are at the same time completely biodegradable, except the substances described ha the patent applications DE 4 3 17 23 1 and EP 0 584 677.

Starch esters are still readily biodegradable at degrees of substitution of more than 1 but can be worked thermoplastically only with difficulty and after the addition of considerable quantities of plasticiser (DE 43 26 118 A1).

The object of the present invention is therefore the synthesis of novel thermoplastic, extrudable and biodegradable polysaccharide esters/polysaccharide ether esters.

This is achieved according to the invention by the esterification of polysaccharides or polysaccharide ethers with maleic anhydride addition products. The preferred maleic anhydride addition products are alkanyl- and/or alkenylsuccinic anhydrides, wherein the alkyl radical optionally containing one or more double bonds preferably has 8 to 18 C atoms, as well as maleic anhydride addition products to isobutylene and polyene fatty acid derivatives. These addition products are known compounds, which are prepared by indirect substituting addition of alpha olefins to maleic anhydride (ensynthesis).

The object is also fulfilled by the synthesis of novel mixed esters from polysaccharides/polysaccharide ethers, maleic anhydride addition products and other dicarboxylic anhydrides such as phthalic anhydride, tetrahydrophthalic anhydride, hexahydrophthalic anhydride or maleic anhydride as well as by the mixed polysaccharide esters/ polysaccharide ether esters from maleic acid addition products and monocarboxylic acids such as acetic acid, propionic acid or butyric acid.

The present invention therefore provides thermoplastic and biodegradable polysaccharide derivatives of polysaccharides or polysaccharide ethers, which are reacted with maleic anhydride addition products, and also polysaccharide esters/polysaccharide ether esters which contain other dicarboxylic acid or monocarboxylic acid groups besides maleic acid addition products.

The polysaccharide ether esters prepared according to the invention can be represented by the general structure

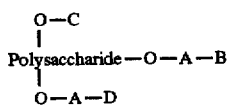

wherein Polysaccharide-O represents the substituted OH groups of a polymeric saccharide unit and wherein A is a linear polyether chain of the following structure

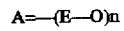

wherein E signifies a linear aliphatic or aromatic branched or unbranched chain having 2 to 11 C atoms, n is an integer equal to or greater than 0 and B is a maleic acid addition product of the following structure

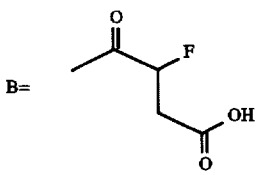

wherein F is an aliphatic, saturated, monounsaturated or polyunsaturated carbon skeleton, which may optionally be provided with further substituents and wherein C can be a hydrogen atom, one or more substituents from the group hydroxyethyl, hydroxypropyl, hydroxybutyl, methyl, ethyl, benzyl, dihydroxypropyl, carboxyalkyl, sulphoalkyl or cyanoethyl.

D is either identical to B or is a carboxylic acid of the structure

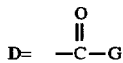

wherein G is an aliphatic C-1 to C-3 carbon skeleton, which may optionally be provided with further substituents or G corresponds to the structure

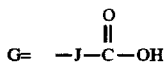

wherein J is an aromatic or aliphatic carbon skeleton, which may optionally be provided with further substituents.

The products according to the invention are in no way comparable with known water-soluble cellulose ethers and starches containing alkanyl- and/or alkenylsuccinic ester groups (EP 024 025 B1), as they are provided with ester groups having higher degrees of substitution (DS) and therefore have completely different sets of properties. They are hydrophobic, soluble in organic solvents and, surprisingly, are thermoplastic and biodegradable.

To synthesise these polysaccharide esters/polysaccharide ether esters from maleic acid addition products, in particular from alkenyl- and/or alkanylsuccinic acid having aliphatic C-8 to C-18 side chains, the polysaccharide derivative is suspended in an organic solvent and the catalyst is added thereto. The maleic anhydride addition product is then added. Examples of suitable catalysts are basic compounds such as, for example, aliphatic, cycloaliphatic and aromatic amines as well as basic inorganic salts. The polysaccharide esters/polysaccharide ether esters thus formed are completely dissolved in the suspension or solution and can be isolated by distilling off the solvent or by precipitation in nonsolvents such as, for example, water.

The reaction temperature of the esterification is between 20° and 150° C., preferably between 80° and 120° C., the reaction time is between 1 and 10 hours, preferably between 2 and 4 hours.

The mixed esters of polysaccharides/polysaccharide esters with maleic acid addition products and other dicarboxylic acids are also obtainable by this route. Thus up to 96.5 mol % of maleic anhydride addition product can be substituted by other polycarboxylic anhydrides without impairing the thermoplasticity and the biodegradability of the products according to the invention. Suitable dicarboxylic anhydrides are phthalic anhydride, tetrahydrophthalic anhydride, maleic anhydride and succinic anhydride. Isatoic anhydride, trimellitic anhydride and pyromellitic anhydride are also suitable.

In the case of polysaccharide esters/polysaccharide ether esters of C-2 to C-4 monocarboxylic acids, in particular of acetic acid, propionic acid and butyric acid, thermoplastic workability with simultaneous biodegradability can be attained when maleic acid addition product groups are additionally introduced.

Examples of suitable polysaccharides are native and soluble starches of any origin, amyloses, amylopectin, alginate, carrageenan, chitin, chitosan, dextran, glycogen, gum, carob-seed grain, laevan, pectin, pollulan, tamarind grain, xanthan and xylan. If polysaccharide ethers are used, suitable compounds are hydroxyethyl starches, hydroxypropyl starches or hydroxypropyl guar, and in particular cellulose ethers such as methyl cellulose, ethyl cellulose, benzyl cellulose, hydroxyethyl cellulose, dihydroxypropyl cellulose, hydroxybutyl cellulose, methylhydroxyethyl cellulose, methylhydroxypropyl cellulose, methylhydroxybutyl cellulose, ethylhydroxypropyl cellulose, ethylhydroxyethyl cellulose, carboxyalkyl cellulose, sulphoalkyl cellulose or cyanoethyl cellulose and mixed ethers thereof having average degrees of substitution (DS) of less than or equal to 1.5, preferably of less than 1.

Suitable suspending media or solvents are ketones, ethers and cyclic ethers, acetals, hydrocarbons and polar aprotic compounds such as dimethyl sulphoxide, dimethylformamide, dimethylacetamide, dioxan, tetrahydrofuran, N-methylmorpholine, N-methylpyrrolidone, dimethoxymethane, dimethyl ether, diethylene glycol dimethyl ether and in addition protonic solvents such as isopropanol, tert.-butanol, acetic acid and, in certain cases, water.

The amines used as catalysts are in particular trimethylamine, triethylamine, tributylamine, tetramethylenediamine, pyridine, N,N-dimethylcyclohexyldiamine, N,N-dimethylbenzylamine, 4-pyrrolidinopyridine, permethyldiethylenetetramine, 1,4-diazabicyclo[2,2,2]octane, 1,8-diazabicyclo[5,4,0]undec-7-ene, 1,5-diazabicyclo[4,3,0]non-5-ene or any mixtures of these.

If basic, inorganic salts are used as catalysts, sodium acetate, sodium carbonate, potassium acetate, potassium carbonate and lithium carbonate are suitable.

In the case of the esterification of cellulose ethers with maleic anhydride addition products and monocarboxylic anhydrides, the reaction can also be catalysed by acids. For this the cellulose ether is suspended in an aliphatic C-2 to C-4 monocarboxylic acid, in particular acetic acid, and an acid catalyst is added thereto. After swelling of the educt, there first of all takes place the addition of the C-2 to C-4 monocarboxylic anhydride, for example, acetic anhydride, propionic anhydride or butyric anhydride, followed by the addition of the maleic acid addition product such as, for example, alkanyl- and/or alkenylsuccinic anhydride. The reaction time is from 1 to 10 hours, in particular 2 to 4 hours, the reaction temperature is from 40° to 80° C., in particular 40° to 50° C., in order to avoid an excessive breakdown of the polysaccharide chains. For working up, aqueous NaOH is added to the homogeneous reaction solution and the solvent is removed either by distillation or by precipitation in water.

Strong mineral acids such as, for example, concentrated sulphuric acid or perchloric acid, are suitable as catalysts.

Suitable solvent/acylating agent combinations are acetic acid/acetic anhydride, propionic acid/propionic anhydride.

The method for the preparation of these derivatives corresponds to the long-known synthesis of cellulose acetate (L. J. Tanghe, L. B. Genung, J. W. Mench, Methods in Carbohydrate Chemistry III, 1963, 193–198), with the advantage that when cellulose ethers are used as educts partially substituted cellulose derivatives are also directly obtainable. It excels moreover by being a less expensive procedure, as the water naturally present in polysaccharide derivatives reacts with the monocarboxylic anhydrides to form the corresponding monocarboxylic acids, which at the same time form the reaction medium. Secondary products can therefore be removed by distillation, which renders unnecessary the further purification both of the product and of the solvent.

By varying the fundamental polysaccharide derivative, the ether component and the ester groups and by selecting the degree of substitution it is possible thus to obtain thermoplastic and biodegradable polysaccharide derivatives having melting points of between 80° and 190° C., which are workable by the conventional processing techniques for thermoplastics such as extrusion, injection moulding or blow moulding.

The products according to the invention display properties which are remarkable and in no way foreseeable. Cellulose acetates are thermoplastic only at a DS of greater than 2.5 and even after addition of considerable quantities of plasticiser still require processing temperatures of >200° C. [F. M üller, Ch. Leuschke in Becker/Braun (Ed.), Kunststoff-Handbuch Volume 3/1: Polycarbonate, Polyacetale, Celluloseester, 1992, 437–445]. Hydroxyalkyl cellulose acetate alkenylsuccinates having a similar degree of substitution, in comparison, already soften without external plasticising at temperatures of below 100° C. Via the nature of the cellulose ether and of the ester components, the variation in the level of substitution and the proportion of alkenylsuccinic anhydride/dicarboxylic acid or C-2 to C-4 monocarboxylic acid, it is possible to obtain polysaccharide esters/polysaccharide ether esters having low degrees of substitution, which nevertheless possess softening points of between 150° and 190° C. typical of workable thermoplastics.

The polysaccharide derivatives according to the invention are suitable for the preparation of, for example, biodegradable sheets, fibres, pots, flasks and other moulded bodies and also as matrix material for formulations for the delayed release of active substances (for example, pheromones, fertilisers, fungicides; insecticides, herbicides or nematocides).

Their properties can be varied via the preparation of blends of any composition with other biodegradable components such as, for example, starches, cellulose, polylactid, glycolid, polyhydroxybutyric acid, polyhydroxyvaleric acid, polycaprolactone, polyester amides or polyester urethanes. Modification by means of auxiliary substances such as, for example, plasticisers, antioxidants, weatherproofing agents, flameproofing agents, dyes or pigments is possible. Moreover compostable anisotropic fibre composites are successfully produced by the introduction of natural fibres such as flax, cellulose, ramie or hemp.

The polysaccharide derivatives described are soluble in organic solvents such as, for example, DMSO, DMAc, dioxan, THF or acetone.

Compared with the known polysaccharide dicarboxylate half esters, the polysaccharide derivatives according to the invention are distinguished by having a number of advantages:

They can be synthesised in ordinary stirred autoclaves of prior art.

The derivatisation can be carried out in organic solvents, with the polysaccharide derivative formed being dissolved.

The derivatives can be recovered in the form of free-flowing thermoplastic powders having a widely adjustable melting range.

The free-flowing powders can be worked thermoplastically in conventional extruders.

Sheets and moulded parts of high quality can be produced economically.

The sheets and mouldings are odourless, water-resistant and fulfil all the performance requirements for conventional materials.

The resulting sheets and mouldings are biodegradable.

The novel polysaccharide ethers/polysaccharide ether esters according to the invention are suitable for the production of moulded parts such as, for example, flasks, flowerpots, disposable cutlery and crockery, golf tees; films for the packaging of food and biological waste; film for mulch; diapers et cetera. They are also suitable for the coating of flat structures such as, for example, paper, mats, woven fabrics, knitted fabrics or other substrates or for the production of fibre blends and laminates. Corresponding materials are also obtainable, for example, from paper recycling.

The quality of the biodegradability is given for the products of Examples 1 to 7 and is investigated in the following manner:

Each 2.5 g of the ground sample was mixed with 20 g of thoroughly rotted compost and 1 ml of water. The mixture was placed in a 1 l flask equipped with a special closure and the air above the mixture was replaced by pure oxygen. After 7, 14 and 28 days the $CO_2$ determination was carried out in the gas phase. After each $CO_2$ determination, the gas phase above the test substance was replaced by pure oxygen. The incubation temperature was 37° C. The evolution of $CO_2$ from positive controls (pulp) and from blank samples (without addition of other biodegradable components) was determined in parallel.

The subject matter of the present invention is explained in more detail by the following Examples.

EXAMPLE 1

A hydroxypropyl cellulose (100 g/0.46 mol) having a degree of substitution (MS) of 0.93 is suspended in 900 g of tert. butanol, 1.2 g of 1,8-diazabicyclo[5,4,0]undec-7-ene (DBU) is added thereto and the reaction mixture is heated to 80° C. After the addition of 233 g (0.88 mol) of 2-dodecenylsuccinic anhydride, the temperature is raised to 120° C., the reaction mixture is stirred for 3 h and the resulting paste-like substance is placed in water. The product precipitated out is washed and dried. It has a softening range of 130°–140° C.

EXAMPLE 2

A hydroxyethyl cellulose (75 g/0.39 mol) having an MS of 0.68 is suspended in 900 g of dioxan, 2.5 g of DBU is added thereto and the reaction mixture is heated at 80° C. for 2 h. After the addition of 86 g (0.59 mol) of phthalic anhydride and 52 g (0.2 mol) of 2-dodecenylsuccinic anhydride, the temperature is raised to 120° C. and maintained there for 3 h, the reaction mixture is cooled and the product is precipitated from water and isolated. The product can be mechanically worked from 210° C.

EXAMPLE 3

75 g (0.39 mol) of a hydroxyethyl cellulose having an MS of 0.68 is suspended in 2000 g of glacial acetic acid, stirred for 2 h at room temperature and 60 g (0.59 mol) of acetic anhydride containing 1 ml of conc. sulphuric acid is added thereto. The reaction mixture is stirred for 1 h at 50° C., then 65 g (0.29 mol) of 2-nonenylsuccinic anhydride is added thereto and, after a further 24 h, 4 ml of 50 per cent aqueous sodium hydroxide solution is added. Evaporation of the solvent, washing with water and drying yields a product having a melting range of 170°–180° C.

EXAMPLE 4

75 g (0.35 mol) of a hydroxypropyl cellulose having an MS of 0.84 is suspended in 2000 g of glacial acetic acid, stirred for 2 h at room temperature and 55 g (0.54 mol) of acetic anhydride containing 1 ml of conc. sulphuric acid is added thereto. The reaction mixture is stirred for 1 h at 50° C., then 72 g (0.27 mol) of 2-dodecenylsuccinic anhydride is added thereto and, after a further 24 h, 4 ml of 50 per cent aqueous sodium hydroxide solution is added. Evaporation of the solvent, washing with water and drying yields a thermoplastic product.

| | |
|---|---|
| MFR 160° C./ 2.16 kg: 1.35 g in 10 min | $O_2$ permeation: 310 cm³/m² d bar (DIN 53380) |
| Modulus of elasticity: 153/121 M Pa (DIN 53457) | $H_2O$ permeation 23° C./85%: 19 g/m² d(DIN 53122) |
| Tear resistance: 7.1 M Pa (DIN 53455) | $CO_2$ evolution after 28 days: 138 mg $CO_2$/g |
| Elongation at break: 28/38% (DIN 53455) | |

EXAMPLE 5

75 g (0.35 mol) of a hydroxypropyl cellulose having an MS of 0.93 is suspended in 1000 g of propionic acid, 1.5 ml of conc. sulphuric acid is added thereto and the reaction mixture is stirred for 1 h at 50° C. After gradual addition of 91 g (0.70 mol) of propionic anhydride and 81 g (0.35 mol) of nonenylsuccinic anhydride, the reaction mixture is stirred for a further 4 h at 50° C., cooled and, after the addition of 5 ml of 50 per cent NaOH, the solvent is evaporated. The thermoplastic isolated melts at 80°–90° C.

EXAMPLE 6

100 g (0.62 mol) of starch is suspended in 1000 g of dimethylsulphoxide, 5 g of DBU is added and the suspension is heated for 1 h at 60° C. After the addition of 100 g (0.38 mol) of 2-dodecenylsuccinic anhydride, the temperature is raised to 80° C. and maintained there for 4 h and the product is subsequently precipitated from water. The resulting starch ester melts at 70°–80° C.

EXAMPLE 7

A suspension of 100 g (0.45 mol) of hydroxypropyl guar (MS approx. 1) in 900 g of dimethylacetamide containing 1.5 g of potassium carbonate is stirred for 1 h at 60° C., 175 g (0.51 mol) of octadecenylsuccinic anhydride is added thereto and heated at 100° C. for 4 h. Precipitation from water yields a derivative which is mechanically workable at 130°–140° C.

We claim:

1. Thermoplastic and biodegradable polysaccharide esters/polysaccharide ether esters represented by the structure

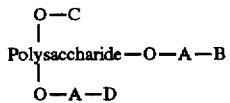

wherein Polysaccharide-O represents the substituted OH groups of a polymeric saccharide unit and wherein A is a linear polyether chain of the following structure

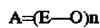

wherein E signifies a linear aliphatic or aromatic branched or unbranched chain having 2 to 11 C atoms, n is an integer equal to or greater than 0 and both B and D are a maleic acid addition product of the following structure

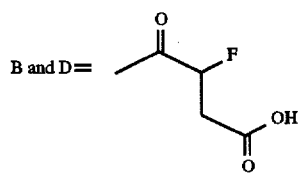

wherein F is an aliphatic, saturated, monounsaturated or polyunsaturated carbon radical and wherein C represents a hydrogen atom or one or more substituents selected from the group consisting of hydroxyethyl, hydroxypropyl, hydroxybutyl, methyl, ethyl, benzyl, dihydroxypropyl, carboxyalkyl, sulphoalkyl and cyanoethyl, wherein said thermoplastic and biodegradable polysaccharide esters/polysaccharide ether esters, per mol of Polysaccharide-O, contain from 0 to 6.5 mol of alkyl ether and from 0.5 to 3 mol of maleic acid addition product.

2. Thermoplastic and biodegradable polysaccharide esters/polysaccharide ether esters according to claim 1, wherein D may additionally be represented by the structure

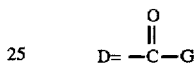

wherein G is an aliphatic C-1 to C-3 carbon radical or

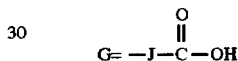

wherein J is an aromatic or aliphatic carbon radical.

3. Thermoplastic and biodegradable polysaccharide esters/polysaccharide ether esters according to claim 1, wherein per mol of polymeric saccharide unit they contain from 0 to 6.5 mol of alkyl ether and X mol of maleic acid addition product as well as Y mol of a monocarboxylic acid or of a further dicarboxylic acid, with the values 0.5<X<2.9, 0.1<Y<2.9 and X+Y<3 applying.

4. Thermoplastic and biodegradable polysaccharide esters/polysaccharide ether esters according to claim 1, wherein the maleic acid addition product groups B and D are alkanyl and/or alkenylsuccinic acid groups having aliphatic C-8 to C-18 side chains.

5. Thermoplastic and biodegradable polysaccharide esters/polysaccharide ether esters according to claim 1, wherein the maleic acid addition product groups B are alkanyl- and/or alkenylsuccinic acid groups having aliphatic C-8 to C-18 side chains.

6. A method for the preparation of thermoplastic and biodegradable polysaccharide esters/polysaccharide ether esters according to claim 1, wherein the esterification reaction used to prepare same is carried out catalyzed by acids, in a monocarboxylic acid as solvent, and the product is isolated by evaporation of the reaction mixture.

7. Moulded parts, sheets, fibres, coatings, blends or laminates comprising at least 10% of the polysaccharide esters/polysaccharide ether esters according to claim 1.

8. In a formulation for the delayed release of an active substance, the formulation containing a matrix material, the improvement wherein the matrix material comprises a thermoplastic and biodegradable polysaccharide ester/polysaccharide ether ester according to claim 1.

9. In the coating of paper by the extruder, dispersion or coating process on by hot melt coating wherein to the paper there is applied a coating material, the improvement wherein the coating material comprises a thermoplastic and biodegradable polysaccharide ester/polysaccharide ether ester according to claim 1.

10. Thermoplastic and biodegradable polysaccharide esters/polysaccharide ether esters according to claim 2, wherein G is an aliphatic C-1 so that $$D= -\overset{O}{\underset{\|}{C}}-G$$

is acetate.

11. Thermoplastic and biodegradable polysaccharide esters/polysaccharide ether esters according to claim 2, wherein J is an aromatic radical so that $$D= -\overset{O}{\underset{\|}{C}}-J-\overset{O}{\underset{\|}{C}}-OH$$

is phthalate.

* * * * *

UNITED STATES PATENT AND TRADEMARK OFFICE
CERTIFICATE OF CORRECTION

PATENT NO. : 5,717,087
DATED : February 10, 1998
INVENTOR(S) : Kalbe, et al.

It is certified that error appears in the above-identified patent and that said Letters Patent is hereby corrected as shown below:

Title Page      ABSTRACT: Line 19 delete " dihydroxyethyl " and substitute -- hydroxyethyl --

Col. 8, line 65      Delete " on "

Signed and Sealed this

Fifth Day of January, 1999

Attest:

Attesting Officer      *Acting Commissioner of Patents and Trademarks*